United States Patent [19]

Geddes et al.

[11] Patent Number: 4,572,206

[45] Date of Patent: Feb. 25, 1986

[54] METHOD AND APPARATUS FOR MEASURING CARDIAC OUTPUT

[75] Inventors: Leslie A. Geddes, West Lafayette, Ind.; David S. Grubbs, Philadelphia, Pa.

[73] Assignee: Purdue Research Foundation, West Lafayette, Ind.

[21] Appl. No.: 370,568

[22] Filed: Apr. 21, 1982

[51] Int. Cl.[4] ............................................. A61B 5/02
[52] U.S. Cl. ..................................... 128/692; 128/713
[58] Field of Search ................................ 128/691–693, 128/713, 734, 632, 642

[56] References Cited

U.S. PATENT DOCUMENTS

| | | | |
|---|---|---|---|
| 3,823,706 | 7/1974 | Davis | 128/691 |
| 3,930,493 | 1/1976 | Williamson | 128/692 |
| 3,985,123 | 10/1976 | Herzlinger et al. | 128/713 |
| 4,015,593 | 4/1977 | Elings et al. | 128/713 |
| 4,175,566 | 11/1979 | Millar | 128/692 |
| 4,380,237 | 4/1983 | Newbower | 128/734 X |

FOREIGN PATENT DOCUMENTS

WO80/0530  4/1980  PCT Int'Appl. .
WO80/01056 3/1982  PCT Int'Appl. .................... 128/692

OTHER PUBLICATIONS

Stewart; "Researches on the Circulation and on the Influences Which Affect It"; *Journ. of Physiology;* 22: 159–83; 1897.
Stewart; "The Output of the Heart in Dogs"; *Amer. Journ. of Physiology;* 57: 27–50; 1921.
Geddes et al.; "Cardiac Output Using an Electrically Calibrated Flow Through Conductivity Cell"; *Journ. of Applied Physiology;* 37: 972-7; 1974.
Geddes et al.; "Elect. Calibration of the Saline Conductivity Method for Cardiac Output: Prelim. Report"; *Cardiovascular Research Center Bulletin;* 10: 91–106; 1972.
Smith et al.; "Cardiac Output Determined by the Saline Conductivity Method Using an Extra-Arterial Conductivity Cell"; *Cardiovascular Research Center Bulletin;* 5: 123–35; 1967.
Geddes et al.; "*Princ. of Applied Biomedical Instrumentation*"; 1975, pp. 330–342.
Smith et al.; "Elect. Calibration for the Saline Dilution Method for Cardiac Output"; *Cardiovascular Research Center Bulletin;* 6: 142–56; 1968.

*Primary Examiner*—Lee S. Cohen
*Assistant Examiner*—Angela D. Sykes
*Attorney, Agent, or Firm*—Woodard, Weikart, Emhardt & Naughton

[57] ABSTRACT

Cardiac output is measured utilizing an indicator, such as saline, which alters blood resistivity, and an electrically calibrated conductivity cell positioned at the tip of a catheter. The catheter with the tetrapolar conductivity cell at the tip is inserted into a blood vessel for current injection to develop a potential which is proportional to blood resistivity for inscribing the dilution curve occurring due to injection of the indicator, which curve is utilized to determine blood flow or cardiac output.

26 Claims, 8 Drawing Figures

METHOD AND APPARATUS FOR MEASURING CARDIAC OUTPUT

FIELD OF THE INVENTION

This invention relates to a method and apparatus for measuring blood flow and, more particularly, relates to measuring cardiac output utilizing an indicator, such as saline, and a conductivity cell positioned at the tip of a catheter.

BACKGROUND OF THE INVENTION

It is often necessary, or at least desirable, that cardiac output be monitored or measured. While apparatus and methods have been heretofore suggested and/or utilized to accomplish this end, such apparatus and/or methods have not been completely satisfactory and have required, for example, mixing of calibrating solutions, withdrawal of blood and/or special preparation of the indicator (such as cooling), which has limited the usefulness of such methods and/or resulting apparatus.

In addition, while dilute saline has heretofore been utilized for the measurement of cardiac output (see, for example, Stewart, G. N. "Researches on the Circulation and on the Influences Which Affect It" *Journ. Physiol.* 22:159–183 (1897) and Stewart, "The Output of the Heart in Dogs" *Amer. Journ. Physiol.* 57:27–50 (1921)), it is now seldom used even though use of such an indicator has attractive features including low cost, low toxicity and enables the use of a simple and inexpensive detector, namely a conductivity cell.

SUMMARY OF THE INVENTION

This invention provides an improved apparatus and method for monitoring and/or measuring cardiac output. A saline indicator and conductivity cell positioned at the tip of a catheter provides an economical yet efficient and dependable apparatus which enables measurement of blood resistivity without the necessity of blood withdrawal or the preparation of calibrating solutions; said blood-resistivity measurement being then utilized for providing the means for calibrating and determining cardiac output.

It is therefore an object of this invention to provide an improved apparatus and method for measuring cardiac output.

It is another object of this invention to provide an improved apparatus and method for measuring cardiac output that does not require blood withdrawal or special preparation of calibrating or indicator solutions.

It is still another object of this invention to provide an improved apparatus and method for measuring cardiac output utilizing an indicator, such as a saline indicator or a poorly conductive indicator such as a 5% dextrose in water (D5W), and a conductivity cell.

It is yet another object of this invention to provide an improved apparatus and method for measuring cardiac output including a saline indicator and a conductivity cell positioned at the tip of a catheter.

It is still another object of this invention to provide an improved apparatus and method for measuring blood resistivity.

With these and other objects in view, which will become apparent to one skilled in the art as the description proceeds, this invention resides in the novel construction, combination, arrangement of parts and method substantially as hereinafter described, and more particularly defined by the appended claims, it being understood that such changes in the precise embodiment of the hereindisclosed invention are meant to be included as come within the scope of the claims.

BRIEF DESCRIPTION OF THE DRAWINGS

The accompanying drawings illustrate a complete embodiment of the invention according to the best mode so far devised for the practical application of the principles thereof, and in which.

DESCRIPTION OF THE INVENTION

Figures 1, 2, 3, 4:
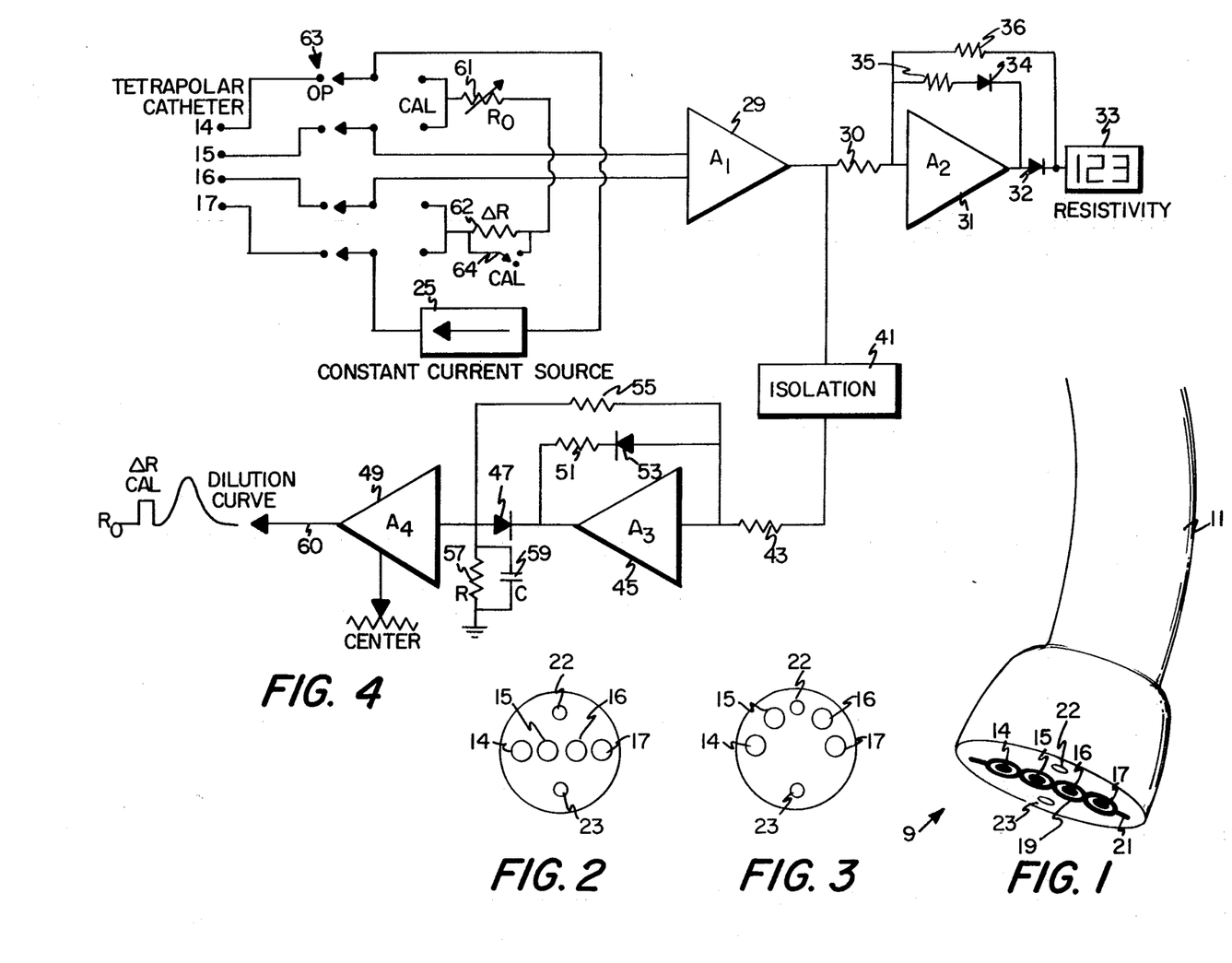
FIG. 1 is a partial perspective view illustrating one typical positioning of a tetrapolar conductivity cell at the tip of a catheter.
FIG. 2 is a front view illustrating the arrangement for the tip of the catheter shown in FIG. 1.
FIG. 3 is a front view illustrating in alternate arrangement of the electrodes at the tip of a catheter.
FIG. 4 is a block and electrical schematic diagram of circuitry used in conjunction with the conductivity cell shown in FIG. 1 to measure blood resistivity continuously and enable recording of the dilution curve.

A sensing unit (tetrapolar conductivity cell) 9, as shown in FIGS. 1 and 2, is contained in a catheter 11. As shown, cell 9 preferably includes a plurality of four electrodes 14, 15, 16 and 17, preferably having insulation 19 therearound, positioned at the end, or tip, 21 of catheter 11. As shown, a pair of lumens 22 and 23 are also provided, which lumens may be utilized for measurement of blood pressure and injection of indicator as well as contrast imaging media, as well as for balloon inflation by means of a third lumen (not shown in FIGS. 1 and 2). FIG. 3 illustrates a different and alternate arrangement of electrodes 14–17. Electrodes 14–17 are useful for pacing and enabling placement in a pulmonary artery by recording the ECG (in addition to acting as a conductivity cell as described herein).

Each electrode (14–17) can be of any convenient material, such as, for example, silver wire, with the end of catheter 11 being heat formed or cemented, so that the four wires (electrodes) are positioned side-by-side or spaced with respect to one another so that the electrodes measure blood resistivity in the axial direction (i.e., across the front of the catheter tip).

Outer electrodes 14 and 17 are connected, as shown in FIG. 4, to an isolated constant-current source 25 which provides the desired current (typically 10 μA, 10 KH$_z$), while the two inner electrodes 15 and 16 are connected to an isolated amplifier 29 for mesurement of a potential which is linearly proportional to blood resistivity.

The output of amplifier 29 is connected through resistor 30 to amplifier 31, the output of which is coupled through diode 32 to a digital display (digital panel meter) 33 (and also fed back to the input side of amplifier 31 through diode 34 and resistor 35 at one side of diode 32, and through resistor 36 at the other side of diode 32). Display 33 provides a direct reading of resistivity multiplied by the cell constant (K) of the catheter-tip conductivity cell 9. The blood resistivity is obtained by dividing the conductivity cell constant (K) into this reading when the catheter is in place for recording the dilution curve.

The output of amplifier 29 is also coupled through isolation circuit 41 and resistor 43 to amplifier 45, the output of which amplifier is coupled through diode 47 to amplifier 49 (and is also fed back to the input side through resistor 51 and diode 53). In addition, the input of amplifier 45 is connected with ground through resistor 55 and parallel connected resistor 57 and capacitor 59. The output from amplifier 49 (on lead 60) is an isolated analog output of blood resistivity the changes of which are the dilution curve.

Calibration of the apparatus is provided by resistors 61 and 62, which as indicated in FIG. 4, are connected into the circuit in lieu of the electrodes of the conductivity cell by changing the positioning of switch 63 from the OP position to the CAL position, and closing CAL switch 64.

It has been heretofore demonstrated (see Geddes, L. A., E. Peery, and R. Steinberg, "Cardiac Output Using an Electrically Calibrated Flow-Through Conductivity Cell," *Journ. Appl. Physiol.* 37:972-977 (1974); Geddes, L. A., C. P. deCosta, and L. E. Baker, "Electrical Calibration of the Saline Conductivity Method for Cardiac Output—A Preliminary Report," *Cardiovasc. Res. Ctr. Bull.* 10:91-106 (1972); and Smith, M. K., L. A. Geddes, and H. E. Hoff, "Cardiac Output Determined by the Saline Conductivity Method Using an Extra-Arterial Conductivity Cell," *Cardiovasc. Res. Ctr. Bull.* 5:123-134 (1967)) that cardiac output can be determined in an animal such as a dog by use of an electrically calibrated flow-through conductivity cell placed in an arteriovenous shunt. The essential information required for electrical calibration was a knowledge of the packed-cell volume, the manner in which blood resistivity decreased with the addition of sodium chloride, and the constant of the conductivity cell used to detect the dilution curve.

It has also been found that one of these requirements, namely the need to draw a blood sample to obtain its packed-cell volume, can be eliminated because the resistivity of blood is dependent on its packed-cell volume (see Geddes, L. A. and L. E. Baker, *Principles of Applied Biomedical Instrumentation* (2nd ed.) New York, Wiley Interscience 1975. 616 pp.). Therefore, the conductivity cell used to obtain the dilution curve can provide this information, as well as serving to detect the dilution curve.

The use of electrical calibration is possible if the manner in which blood decreases its resistivity with added sodium chloride ($\Delta\rho/\Delta C$) is known. This information has been heretofore reported for a variety of species (see Geddes, L. A. and L. E. Baker, *Principles of Applied Biomedical Instrumentation* (2nd Ed.) New York, Wiley Interscience 1975. 616 pp.). Therefore, if the conductivity cell constant (K) is known, it is possible to insert a resistance change ($\Delta R$) into the resistivity-measuring circuit and equate the resistance change to a concentration change ($\Delta C$) as follows:

$$\Delta C = \frac{\Delta R}{K(\Delta\rho/\Delta C)} \tag{1}$$

where $\Delta C$ is the concentration change equivalent to the resistance change $\Delta R$; K is the conductivity cell constant and $\Delta\rho/\Delta C$ is the manner in which blood resistivity decreases with added sodium chloride.

$\Delta\rho/\Delta C$ is a fundamental property of blood and depends on packed-cell volume (H) according to:

$$\Delta\rho/\Delta C = Ae^{\alpha H} \tag{2}$$

where A and $\alpha$ are constants and H is the packed-cell volume. Values for A and $\alpha$ for a variety of animal species are shown, for example, in, Geddes, L. A. and L. E. Baker, *Principles of Applied Biomedical Instrumentation* (2nd ed.) New York, Wiley Interscience 1975, 616 pp.

However, it is well known that the resistivity of blood ($\rho$) is a function of its packed-cell volume (H). Many different expressions have been used, the simplest being:

$$\rho = Be^{\beta H} \tag{3}$$

where $\rho$ is the resistivity of blood, H is the packed-cell volume and B and $\beta$ are constants, the values for which have been heretofore summarized (see Geddes, L. A. and L. E. Baker, *Principles of Applied Biomedical Instrumentation* (2nd ed.) New York, Wiley Interscience 1975. 616 pp.).

It is possible to eliminate H from these two equations and obtain the following:

$$\Delta\rho/\Delta C = \frac{A\rho^{\alpha/\beta}}{B^{\alpha/\beta}} \tag{4}$$

Therefore, by knowing the resistivity of the blood ($\rho$), a value for $\Delta\rho/\Delta C$ can be obtained. Note that a log-log plot of equation 4 will be a straight line (see FIG. 5).

Figure 5:
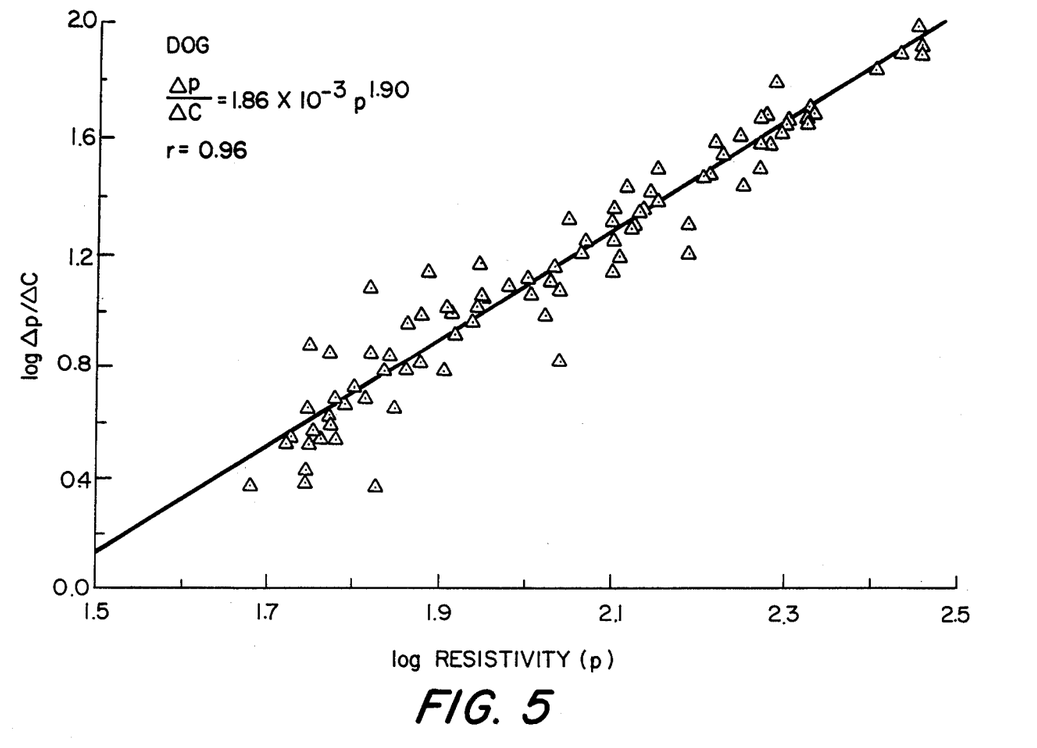
FIG. 5 is a graph illustrating the relationship between $\Delta\rho/\Delta c$ and $\rho$ the resistivity of dog blood, and wherein $\Delta\rho/\Delta c$ is the quantity used to calibrate the dilution curve.

Measured values for $\Delta\rho/\Delta C$ and $\rho$ heretofore obtained (see Geddes, L. A., E. Perry, and R. Steinberg, "Cardiac Output Using an Electrically Calibrated Flow-Through Conductivity Cell," *Journ. Appl. Physiol.* 37:972-977 (1974) were plotted and a log-log, least-squares representation was obtained (FIG. 5) to provide the following fundamental electrical calibration relationship for dog blood:

$$\Delta\rho/\Delta C = 1.86 \times 10^{-3} \rho^{1.90} \tag{5}$$

where $\Delta\rho/\Delta C$ is in ohm-cm/gm per liter and $\rho$, the blood resistivity, is in ohm-cm. FIG. 5 presents this relationship graphically for dog blood. A similar relationship exists for human blood.

The conductivity cell constant (K) is easily determined by measuring the resistivity of a known solution, e.g. 0.6% NaCl. The resistivity of such a solution was measured with a platinum-black electrode connected to a conductivity bridge (Yellow Springs Instruments, Yellow Springs, OH). Once the value for K has been determined, it need not be remeasured. The value for K is therefore: K = R catheter/$\rho$ platinum-black electrode, where R catheter is the 1 KHz resistance, and $\rho$ is the resistivity of the known calibrate solution.

To test the device of this invention, ten dogs, ranging in weight from 13.5 to 32.5 kg were used. Pentobarbital sodium (30 mg/kg i.v.) was used and the trachea was intubated with a cuffed tube. Data were obtained with normal, elevated and reduced cardiac output. Cardiac output was raised with an i.v. drip of epinephrine and lowered by controlled hemorrhage.

Cardiac output was also measured by means of the known Fick method. For this method, the oxygen uptake was measured with an oxygen-filled spirometer containing a carbon-dioxide absorber. The spirometer was connected to the tracheal tube by a one-way breathing value. Oxygen uptake was measured for five minutes to obtain a stable value which was recorded on a stripchart recorder. Blood samples were taken from a femoral artery (arterial sample) and a catheter advanced to the apex of the right ventricle (venous sample). The samples were analyzed for oxygen content with the Lex-$O_2$-Con (Lexington Instruments, Waltham, MA). Since this device provides data at STP dry, the oxygen uptake measured with the spirometer was converted to STP dry with the gas law. Cardiac output (CO) was calculated from the known equation:

$$CO = \text{oxygen uptake per min/A-V Oxygen difference TM} \qquad (6)$$

To inscribe the dilution curve, the tetrapolar cell 9 was advanced down the jugular vein into the pulmonary artery. From the digital reading on the recording equipment, blood resistivity was calculated by dividing the cell constant into this reading. The value of $\Delta\rho/\Delta C$ was then calculated utilizing the graph of FIG. 5. The dilution curve was recorded by injecting a 2 ml of 5% saline into the right ventricle.

Figure 6:
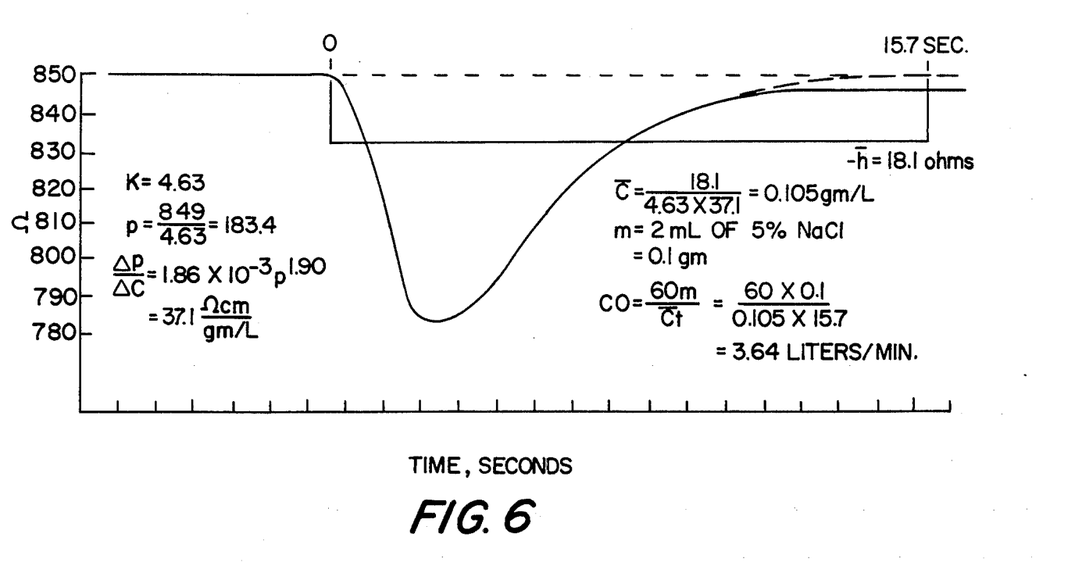
FIG. 6 is a typical dilution curve corrected for recirculation and sample calculation of cardiac output using $\rho$ and $\Delta\rho/\Delta c$ to calculate the conductivity cell having a constant k.

The dilution curve was calibrated in ohms by substituting a decade resistor for the tetrapolar conductivity cell. FIG. 6 illustrates a typical dilution curve obtained by injecting 2 ml of 5% saline into the right atrium. The mean height (h) in ohms of the dilution curve is converted to mean concentration as follows:

$$C = \frac{h}{k(\Delta\rho/\Delta C)} \qquad (7)$$

The dilution curves were digitized manually with a Graf Pen (Science Accessories Corp., Southport, CN) and entered into a PDP-11/03 digital computer programmed to perform a semilog extrapolation to correct the dilution curve for recirculation. The area, mean height and length of the dilution curves were read out and converted to mean concentration (by scaling as shown in FIG. 6). Cardiac output was calculated from:

$$CO = 60 \, m/Ct \qquad (8)$$

where m is the number of grams of sodium chloride injected, C is the mean concentration and t is the duration of the corrected dilution curve in seconds. Although FIG. 6 illustrates a dilution curve obtained by injecting saline (i.e., an indicator having a higher conductivity than blood), it is to be realized that other indicators can be utilized such as, for example, a 5% dextrose in water (D5W) i.e., an indicator having a lower conductivity than blood).

Figure 7:
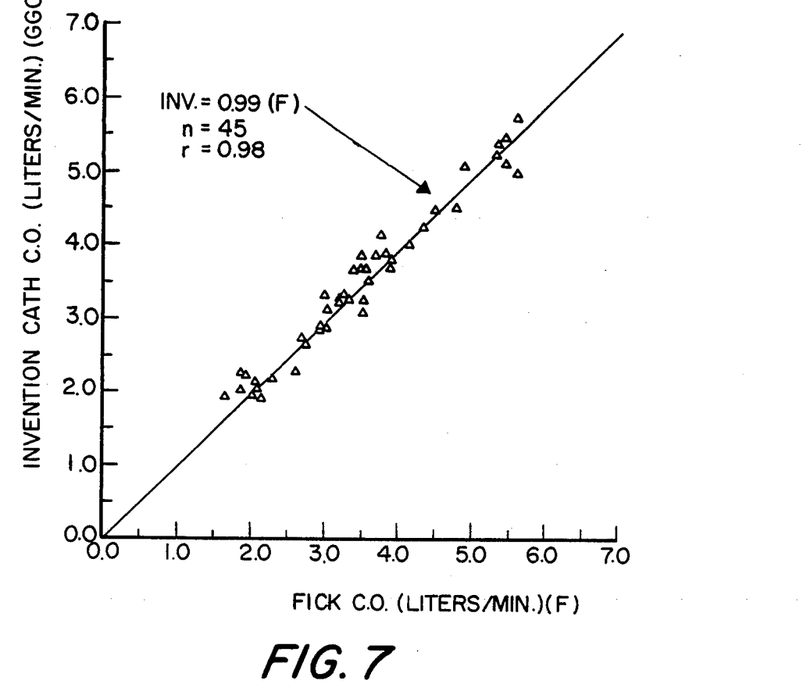
FIG. 7 is a graph illustrating cardiac output in the dog determined with the catheter tip transducer in the pulmonary artery and values, for comparison, obtained with the direct Fick method.

FIG. 7 presents the relationship between cardiac output obtained with the electrically calibrated conductivity cell and the direct-Fick method. The dashed line represents the equal-value line and the solid line is the linear regression line for all of the data points. It is clear that the saline method provides slightly higher values for cardiac output that are very close to those obtained with the Fick method. For all paired data points, the average value of the saline method underestimated the cardiac output by one percent.

This invention can be utilized for hemodilutions by adding saline with a resistivity equal to that of plasma. Use of the apparatus shown in FIGS. 1, 2 and 4 for recording conductivity in the pulmonary artery is shown in FIG. 8.

Figure 8:
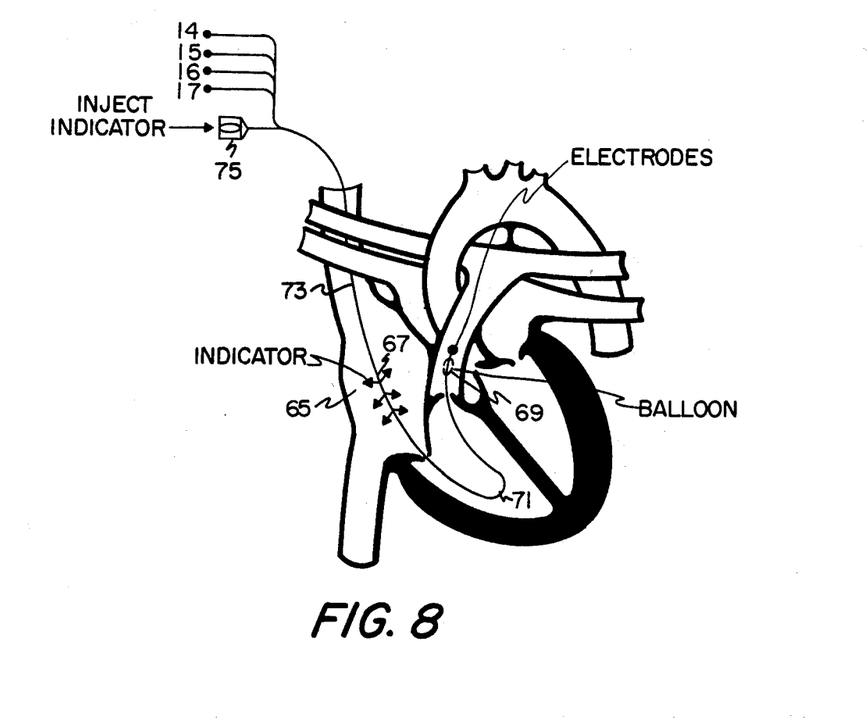
FIG. 8 is a partial cut-away perspective view illustrating positioning of the device of this invention in the pulmonary artery.

With respect to use as shown in FIG. 8, only a single vessel (arm vein) 65 need be used to insert the apparatus into the pulmonary artery. Catheter 67 preferably includes a balloon 69 for flow guidance, a first lumen (generally indicated by the numeral 71) for balloon inflation, and a second lumen (generally indicated by the numeral 73) for injecting the indicator (by means of inject fitting 75) connected with an inlet port (not shown). In the preferred embodiment, a third lumen is also included for recording pressure; but such a pressure lumen is not necessary for catheter placement. The identification of the location of the catheter tip is made by recording the electrocardiogram from the catheter electrode and an indifferent electrode placed at any convenient site on the subject. The electrodes 14–17 positioned at the tip of the catheter provide outputs (indicated by the numerals 14–17) which are coupled to the circuitry as shown in FIG. 2 for measuring the blood resistivity and inscribing the dilution curve in the same manner as described hereinabove.

From the foregoing, it can be appreciated that this invention provides an apparatus and method for use of an indicator such as saline and a detector such as a catheter conductivity cell that does not require withdrawal of blood to make calibration solutions for the detector or to measure packed-cell volume to determine a value for $\Delta\rho/\Delta C$, the manner in which blood resistivity decreases with the addition of the indicator, and does not require that the conductivity cell be kept warm since it is inside the body. Multiple dilution curves can therefore be recorded every few minutes if desired without blood loss and electrical calibration of the dilution curve can be achieved without the need for preparing calibrating samples.

What is claimed is:

1. An indicator-dilution method for measuring cardiac output, said method comprising:
    placing a conductivity cell in the flow path of blood;
    electrically calibrating said conductivity cell without withdrawing blood from said flow path, said calibrating being accomplished by utilizing said conductivity cell to generate an output indicative of baseline blood resistivity;
    injecting an indicator into said blood flow path and obtaining an output signal from said conductivity cell indicative of blood resistivity as altered by said indicator; and
    determining cardiac output from said output indicative of baseline blood resistivity and said output signal indicative of altered blood resistivity.

2. The method of claim 1 wherein said conductivity cell is positioned at the end of a catheter.

3. The method of claim 2 wherein said catheter is inserted into a blood vessel so that said conductivity cell is in the flow path of blood in said vessel.

4. The method of claim 1 wherein said method includes generating an electrical signal and coupling the same to said conductivity cell, developing a potential at said conductivity cell responsive to said generated electrical signal, and utilizing said developed potential to generate said output indicative of baseline blood resistivity and said output signal indicative of altered blood resistivity.

5. The method of claim 1 wherein said method includes developing a dilution curve based upon said output signal indicative of altered blood resistivity, converting said dilution curve to mean concentration, and determining said cardiac output from said mean concentration.

6. The method of claim 5 wherein said injected indicator is a saline solution.

7. An indicator-dilution method for measuring cardiac output, said method comprising:
positioning a detector on a catheter;
inserting said catheter into a body such that said detector is in the flow path of blood in said body;
electrically calibrating said detector without withdrawing blood from said body, said calibrating including electrically exciting said detector so that said detector provides an output indicative of baseline blood resistivity;
injecting an indicator into said blood flow path and electrically exciting said detector so that said detector provides an output signal indicative of blood resistivity as altered by said indicator; and
determining cardiac output from said output indicative of baseline blood resistivity and said output signal indicative of altered blood resistivity.

8. The method of claim 7 wherein said detector is a tetrapolar conductivity cell, and wherein said method includes electrically exciting a first pair of poles of said tetrapolar conductivity cell to develop a potential indicative of baseline blood resistivity on a second pair of poles of said tetrapolar conductivity cell.

9. The method of claim 8 wherein said electrical excitation is provided by a constant-current source.

10. The method of claim 8 wherein said output indicative of baseline blood resistivity is developed by dividing said potential indicative of baseline blood resistivity by the cell constant of said conductivity cell.

11. The method of claim 8 wherein said detector is excited by providing a current to said first pair of poles from a constant-current source.

12. The method of claim 7 wherein said method includes inscribing a dilution curve from said output signal indicative of altered blood resistivity, calibrating said dilution curve in ohms, converting said dilution curve to mean concentration, and determining cardiac output from said mean concentration.

13. The method of claim 12 wherein said injected indicator is an indicator having a higher conductivity than blood.

14. The method of claim 13 wherein said indicator is a saline solution.

15. The method of claim 12 wherein said injected indicator is an indicator having a lower conductivity than blood.

16. The method of claim 15 wherein said indicator is 5% dextrose in water.

17. An apparatus for enabling measurement of cardiac output by determination of blood resistivity, said apparatus comprising:
detector means for detecting resistivity;
positioning means for adapting said detector means to be positioned in the flow path of blood;
electrical means connected with said detector means for generating an output that is proportional to the resistivity of the blood in said flow path, said electrical means including means for generating an output indicative of baseline blood resistivity, and calibration means for electrically calibrating said apparatus, said calibration means including baseline calibration means for calibrating said output indicative of baseline blood resistivity.

18. The apparatus of claim 17 wherein said apparatus includes indicating means for receiving said output from said electrical means and indicating said blood resistivity.

19. The apparatus of claim 18 wherein said indicating means includes a digital readout device.

20. The apparatus of claim 18 wherein said indicating means includes means for enabling inscribing of a dilution curve.

21. The apparatus of claim 17 wherein said detector means is a conductivity cell having a plurality of electrodes, and wherein said positioning means includes a catheter having said conductivity cell positioned at the tip thereof and means for preventing said electrodes from contacting a wall defining the flow path of blood.

22. The apparatus of claim 21 wherein said conductivity cell is a tetrapolar conductivity cell.

23. The apparatus of claim 22 wherein said tetrapolar conductivity cell includes a pair of exciting electrodes and a pair of output electrodes, and wherein said electrical means includes a constant-current source connected with said exciting electrodes.

24. The apparatus of claim 21 wherein said conductivity cell has four electrodes arranged along said tip of said catheter in a plane perpendicular to the longitudinal axis of said catheter.

25. The apparatus of claim 21 wherein said catheter is adapted for insertion in a blood vessel, has an inflatable balloon therein, and at least a first lumen for inflation of said balloon and a second lumen for injecting indicator.

26. An apparatus for enabling measurement of cardiac output by determination of blood resistivity, said apparatus comprising:
a tetrapolar conductivity cell having four electrodes;
a catheter having said conductivity cell positioned on the tip thereof, said catheter being adapted for insertion into a body so that said conductivity cell is in the flow path of blood in said body;
a constant-current source connected with two of said electrodes of said conductivity cell;
first amplifying means connected with the other two of said electrodes of said conductivity cell for amplifying a potential appearing on said electrodes;
indicating means connected with said first amplifying means for indicating resistivity;
isolation means connected with said first amplifying means for providing signal isolation; and
second amplifying means connected with said isolation means and providing an isolated analog output of blood resistivity for enabling inscribing of the dilution curve of blood resistivity,
wherein said four electrodes are spaced with respect to one another in a line along the end of the tip of said catheter, and wherein the outer two of said electrodes are connected with said constant-current source and the inner two of said electrodes are connected with said first amplifying means.

* * * * *

REEXAMINATION CERTIFICATE (1399th)
United States Patent
[11] B1 4,572,206

Geddes et al.

[45] Certificate Issued  Jan. 1, 1991

[54] METHOD AND APPARATUS FOR MEASURING CARDIAC OUTPUT

[75] Inventors: Leslie A. Geddes, West Lafayette, Ind.; David S. Grubbs, Philadelphia, Pa.

[73] Assignee: Purdue Research Foundation

Reexamination Request:
No. 90/001,814, Jul. 26, 1989

Reexamination Certificate for:
Patent No.: 4,572,206
Issued: Feb. 25, 1986
Appl. No.: 370,568
Filed: Apr. 21, 1982

[51] Int. Cl.$^5$ ............................................. A61B 5/02
[52] U.S. Cl. .................................... 128/692; 128/713
[58] Field of Search ................................ 128/691–693, 128/713, 734, 632, 642

[56] References Cited

U.S. PATENT DOCUMENTS

4,380,237  4/1983  Newbower ..................... 128/693

FOREIGN PATENT DOCUMENTS

2819128  11/1979  Fed. Rep. of Germany .

OTHER PUBLICATIONS

Smith et al, "Cardiac Output Determined by the Saline Conductivity Method Using an Extra-Arterial Conductivity Cell", Cardio. Res. Ctr. Bull. 5, 123–5 (1967).

Geddes/Baker, "Principles of Applied Biomedical Instrumentation, Second Edition", pp. 330–342 (1975).

A. Van Oosterom et al, "Intramural Resistivity of Cardiac Tissue", Med. & Biol. Eng. & Comput., May 1979, pp. 337–343.

Bourdillon et al, "Saline Conductivity Method for Measuring Cardiac Output Simplified", Med. & Biol. Eng. & Comput., 1979, pp. 323–329.

Constantinesco et al, "Intravascular Mean Blood Velocity Measurements Using a Crosscorrelation Technique", Med. & Biol. Eng. & Comput., pp. 439–446 (1980).

D. S. Grubbs et al, "A New Technique for Obtaining Values of Cardiac Output in Rapid Succession", IEEE Transactions on Biomedical Engineering, vol. BME-29, No. 12, pp. 769–777, (Dec. 1982).

*Primary Examiner*—Lee S. Cohen

[57] ABSTRACT

Cardiac output is measured utilizing an indicator, such as saline, which alters blood resistivity, and an electrically calibrated conductivity cell positioned at the tip of a catheter. The catheter with the tetrapolar conductivity cell at the tip is inserted into a blood vessel for current injection to develop a potential which is proportional to blood resistivity for inscribing the dilution curve occurring due to injection of the indicator, which curve is utilized to determine blood flow or cardiac output.

__B1 4,572,206__

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claim 26 is confirmed.

Claims 1, 7, and 17 are determined to be patentable as amended.

Claims 2–6, 8–16, 18–25, dependent on an amended claim, are determined to be patentable.

New claims 27–38 are added and determined to be patentable.

1. An indicator-dilution method for measuring cardiac output, said method comprising:
   placing a conductivity cell in the flow path of blood;
   electrically calibrating said conductivity cell without withdrawing blood from said flow path, said calibrating being accomplished by utilizing said conductivity cell to generate an output indicative of baseline blood resistivity, *said calibrating being based on a predetermined relationship between $\Delta p/\Delta C$ and blood resistivity for the subject species;*
   injecting an indicator into said blood flow path and obtaining an output signal from said conductivity cell indicative of blood resistivity as altered by said indicator; and
   determining cardiac output from said output indicative of baseline blood resistivity and said output signal indicative of altered blood resistivity.

7. An indicator-dilution method for measuring cardiac output, said method comprising:
   positioning a detector on a catheter;
   inserting said catheter into a body such that said detector is in the flow path of blood in said body;
   electrically calibrating said detector without withdrawing blood from said body, said calibrating including electrically exciting said detector so that said detector provides an output indicative of baseline blood resistivity, *said calibrating being based on a predetermined relationship between $\Delta p/\Delta C$ and blood resistivity for the subject species;*
   injecting an indicator into said blood flow path and electrically exciting said detector so that said detector provides an output signal indicative of blood resistivity as altered by said indicator; and
   determining cardiac output from said output indicative of baseline blood resistivity and said output signal indicative of altered blood resistivity.

17. An apparatus for enabling measurement of cardiac output by determination of blood resistivity, said apparatus comprising:
    detector means for detecting resistivity;
    positioning means for adapting said detector means to be positioned in the flow path of blood;
    electrical means connected with said detector means for generating an output that is proportional to the resistivity of the blood in said flow path, said electrical means including means for generating an output indicative of baseline blood resistivity, and calibration means for electrically calibrating said apparatus *based on a predetermined relationship between $\Delta p/\Delta C$ and blood resistivity for the subject species,* said calibration means including baseline calibration means for calibrating said output indicative of baseline blood resistivity.

27. *An indicator-dilution method for measuring cardiac output, said method comprising:*
    *placing a conductivity cell in the flow path of blood;*
    *electrically calibrating said conductivity cell without withdrawing blood from said flow path and without varying hematocrit, said calibrating being accomplished by utilizing said conductivity cell to measure baseline blood resistivity, said calibrating being performed with a conductivity cell constant defined by the ratio of resistance to resistivity for said conductivity cell;*
    *injecting an indicator into said blood flow path and measuring blood resistivity as altered by said indicator; and*
    *determining cardiac output from said baseline blood resistivity and said altered blood resistivity.*

28. *The method of claim 27 wherein said conductivity cell is positioned at the end of a catheter, and wherein said method includes generating an electrical signal and coupling the same to said conductivity cell, developing a potential at said conductivity cell responsive to said generated electrical signal, and utilizing said developed potential to generate said baseline blood resistivity and said altered blood resistivity.*

29. *The method of claim 27 wherein said method includes converting said altered blood resistivity to mean concentration and determining said cardiac output from said mean concentration.*

30. *An indicator-dilution method for measuring cardiac output, said method comprising:*
    *positioning a detector on a catheter;*
    *inserting said catheter into a body such that said detector is in the flow path of blood in said body;*
    *electrically calibrating said detector without withdrawing blood from said body and without varying hematocrit, said calibrating including electrically exciting said detector so that said detector provides an output indicative of baseline blood resistivity, said calibrating being performed with a conductivity cell constant defined by the ratio of resistance to resistivity for said conductivity cell;*
    *injecting an indicator into said blood flow path and electrically exciting said detector so that said detector provides an output signal indicative of blood resistivity as altered by said indicator; and*
    *determining cardiac output from said output indicative of baseline blood resistivity and said output signal indicative of altered blood resistivity.*

31. *The method of claim 30 wherein said detector is a tetrapolar conductivity cell, and wherein said method includes electrically exciting a first pair of poles of said tetrapolar conductivity cell to develop a potential indicative of baseline blood resistivity on a second pair of poles of said tetrapolar conductivity cell.*

32. The method of claim 31 wherein said output indicative of baseline blood resistivity is developed by dividing said potential indicative of baseline blood resistivity by the cell constant of said conductivity cell.

33. The method of claim 31 wherein said detector is excited by providing a current to said first pair of poles from a constant-current source.

34. The method of claim 30 wherein said method includes determining mean concentration from said output signal indicative of altered blood resistivity, and determining said cardiac output from said mean concentration.

35. An apparatus for enabling measurement of cardiac output by determination of blood resistivity, said apparatus comprising:
   detector means for detecting resistivity;
   means for determining a cell constant defined by the ratio of resistance to resistivity for said detector means;
   positioning means for adapting said detector means to be positioned in the flow path of blood;
   electrical means connected with said detector means for generating an output that is proportional to the resistivity of the blood in said flow path, said electrical means including means for generating an output indicative of baseline blood resistivity, and calibration means for electrically calibrating said apparatus without varying hematocrit, said calibration means including baseline calibration means for calibrating said output indicative of baseline blood resistivity.

36. The apparatus of claim 35 wherein said detector means is a conductivity cell having a plurality of electrodes, and wherein said positioning means includes a catheter having said conductivity cell positioned at the tip thereof and means for preventing said electrodes from contacting a wall defining the flow path of blood.

37. The apparatus of claim 36 wherein said conductivity cell is a tetrapolar conductivity cell having a pair of exciting electrodes and a pair of output electrodes, and wherein said electrical means includes a constant-current source connected with said exciting electrodes.

38. The apparatus of claim 36 wherein said conductivity cell has four electrodes arranged along said tip of said catheter in a plane perpendicular to the longitudinal axis of said catheter.

* * * * *